US010962929B2

(12) United States Patent
Delgado et al.

(10) Patent No.: US 10,962,929 B2
(45) Date of Patent: Mar. 30, 2021

(54) INTERFERENCE OPTICS FOR OPTICAL IMAGING DEVICE

(71) Applicant: Open Water Internet Inc., San Francisco, CA (US)

(72) Inventors: Edgar Emilio Morales Delgado, San Francisco, CA (US); Caitlin Regan, Sausalito, CA (US); Mary Lou Jepsen, Sausalito, CA (US); Craig Newswanger, Oakland, CA (US); Sarmishtha Satpathy, San Francisco, CA (US)

(73) Assignee: Open Water Internet Inc., San Francisco, CA (US)

( * ) Notice: Subject to any disclaimer, the term of this patent is extended or adjusted under 35 U.S.C. 154(b) by 229 days.

(21) Appl. No.: 16/204,940

(22) Filed: Nov. 29, 2018

(65) Prior Publication Data
US 2020/0089165 A1 Mar. 19, 2020

Related U.S. Application Data

(60) Provisional application No. 62/731,308, filed on Sep. 14, 2018.

(51) Int. Cl.
*G03H 1/00* (2006.01)
*G03H 1/04* (2006.01)
(Continued)

(52) U.S. Cl.
CPC ......... *G03H 1/0443* (2013.01); *A61B 5/0051* (2013.01); *A61B 5/0066* (2013.01);
(Continued)

(58) Field of Classification Search
CPC ............... G03H 1/0443; G03H 1/0465; G03H 2001/0452; G03H 2222/16; G03H 2223/16; G03H 2223/23; G03H 2223/2223; G03H 2223/24; G03H 2223/53; G03H 1/00; G03H 1/0005; G03H 2001/0083; G03H 2001/0204; G03H 1/08; G03H 1/0866; G03H 1/26; G03H 2001/2605;
(Continued)

(56) References Cited

U.S. PATENT DOCUMENTS 6,172,760 B1 1/2001 Son
6,956,650 B2 10/2005 Boas
(Continued)

OTHER PUBLICATIONS

Arridge et al. Nonuniqueness in diffusion-based optical tomography, Optics Letters, Jun. 1, 1998, vol. 23, No. 11, pp. 882-884.
(Continued)

*Primary Examiner* — Arnel C Lavarias
(74) *Attorney, Agent, or Firm* — Freestone Intellectual Property Law PLLC; Aaron J. Visbeek

(57) ABSTRACT

A device includes a sensor, a coherent infrared illumination source and optics to direct an infrared reference beam to the sensor. The sensor is positioned to capture an image of an interference signal generated by an interference of the infrared reference beam and a wavelength-shifted exit signal. The wavelength-shifted exit signal propagates through the optics before interfering with the infrared reference beam.

13 Claims, 11 Drawing Sheets

(51) Int. Cl.
　　　*A61B 5/00*　　　(2006.01)
　　　*A61B 8/00*　　　(2006.01)
　　　*H04N 5/33*　　　(2006.01)

(52) U.S. Cl.
　　　CPC ............ *A61B 5/0097* (2013.01); *A61B 5/745* (2013.01); *A61B 8/463* (2013.01); *G03H 1/0465* (2013.01); *H04N 5/33* (2013.01); *A61B 2562/0238* (2013.01); *G03H 2001/0452* (2013.01); *G03H 2222/16* (2013.01); *G03H 2223/16* (2013.01); *G03H 2223/23* (2013.01); *G03H 2223/24* (2013.01); *G03H 2223/53* (2013.01)

(58) Field of Classification Search
　　　CPC ... A61B 5/0051; A61B 5/0066; A61B 5/0097; A61B 5/745; A61B 8/463; A61B 2562/0238; H04N 5/33
　　　USPC ................... 359/30, 1, 9, 22, 25, 28, 32, 35; 356/450, 457, 484
　　　See application file for complete search history.

(56) References Cited

U.S. PATENT DOCUMENTS

| | | |
|---|---|---|
| 7,119,906 B2 | 10/2006 | Pepper |
| 7,460,248 B2 | 12/2008 | Kurtz |
| 7,551,809 B2 | 6/2009 | Taira |
| 7,610,082 B2 | 10/2009 | Chance |
| 7,647,091 B2 | 1/2010 | Ntziachristos |
| 7,728,986 B2 | 6/2010 | Lasker |
| 7,773,229 B2 * | 8/2010 | Harlander ................. G01P 5/26 356/451 |
| 7,804,070 B1 | 9/2010 | Pan |
| 7,821,640 B2 | 10/2010 | Koenig |
| 7,822,468 B2 | 10/2010 | Stamnes |
| 7,826,878 B2 | 11/2010 | Alfano |
| 7,898,649 B2 | 3/2011 | Masumura |
| 7,965,389 B2 | 6/2011 | Da Silva |
| 7,983,740 B2 | 7/2011 | Culver |
| 7,928,896 B2 | 8/2011 | Jin |
| 8,014,847 B2 | 9/2011 | Shastri |
| 8,120,784 B2 | 2/2012 | Da Silva |
| 8,170,651 B2 | 5/2012 | Lorenzo |
| 8,239,006 B2 | 8/2012 | Zhu |
| 8,263,947 B2 | 9/2012 | Da Silva |
| 8,289,502 B2 | 10/2012 | Yoshida |
| 8,326,567 B2 | 12/2012 | Masumura |
| 8,330,642 B2 | 12/2012 | Jin |
| 8,355,131 B2 | 1/2013 | Bakker |
| 8,357,915 B2 | 1/2013 | Guyon |
| 8,374,409 B2 | 2/2013 | Jochemsen |
| 8,416,421 B2 | 4/2013 | Wang |
| 8,450,674 B2 | 5/2013 | Yang |
| 8,451,450 B2 | 5/2013 | Heng |
| 8,520,921 B2 | 8/2013 | Ziegler |
| 8,525,998 B2 | 9/2013 | Yaqoob |
| 8,527,242 B2 | 9/2013 | Granot |
| 8,531,662 B2 | 9/2013 | Van Der Mark |
| 8,563,932 B2 | 10/2013 | Fang |
| 8,634,077 B2 | 1/2014 | Hu |
| 8,649,015 B2 | 2/2014 | Ichihara |
| 8,917,442 B2 | 3/2014 | Baym |
| 8,717,574 B2 | 5/2014 | Yang |
| 8,814,795 B2 | 8/2014 | Derode |
| 8,817,255 B2 | 8/2014 | Masumura |
| 8,830,573 B2 | 9/2014 | Cui |
| 8,847,175 B2 | 9/2014 | Laidevant |
| 8,937,284 B2 | 1/2015 | Fang |
| 8,954,130 B2 | 2/2015 | Masumura |
| 8,976,433 B2 | 3/2015 | Masumura |
| 9,012,869 B2 | 4/2015 | Andersson-Engels |
| 9,036,970 B2 | 5/2015 | Guyon |
| 9,037,216 B2 | 5/2015 | Hielscher |
| 9,057,695 B2 | 6/2015 | Masumura |
| 9,131,851 B2 | 9/2015 | Fukutani |
| 9,134,229 B2 | 9/2015 | Lesage |
| 9,179,842 B2 | 11/2015 | Nakaji |
| 9,207,171 B2 | 12/2015 | Nadakuditi |
| 9,234,841 B2 | 1/2016 | Wang |
| 9,282,932 B2 | 3/2016 | Kudo |
| 9,297,752 B2 | 3/2016 | Shimokawa |
| 9,304,490 B2 | 4/2016 | Masumura |
| 9,313,423 B2 | 4/2016 | Wang |
| 9,335,604 B2 | 5/2016 | Popovich |
| 9,335,605 B2 | 5/2016 | Wang |
| 9,341,569 B2 | 5/2016 | Hooft |
| 9,354,166 B2 | 5/2016 | Judkewitz |
| 9,373,020 B2 | 6/2016 | Kudo |
| 9,407,796 B2 | 8/2016 | Dinten |
| 9,427,213 B2 | 8/2016 | Suzuki |
| 9,480,425 B2 | 11/2016 | Culver |
| 9,486,142 B2 | 11/2016 | Hielscher |
| 9,488,574 B2 | 11/2016 | Koehler |
| 9,509,956 B2 | 11/2016 | Piestun |
| 9,622,663 B2 | 4/2017 | Fang |
| 9,689,797 B2 | 6/2017 | Sun |
| 9,724,489 B2 | 8/2017 | Barbour |
| 9,730,649 B1 | 8/2017 | Jepsen |
| 9,750,413 B2 | 9/2017 | Sandusky |
| 2008/0068722 A1 * | 3/2008 | Chow ................. G01B 11/0625 359/629 |
| 2010/0016732 A1 | 1/2010 | Wells |
| 2012/0070817 A1 | 3/2012 | Wang et al. |
| 2014/0081296 A1 | 3/2014 | Baym |
| 2014/0114181 A1 | 4/2014 | Wu |
| 2014/0303473 A1 | 10/2014 | Nanaumi |
| 2015/0182121 A1 | 7/2015 | Barbour |
| 2015/0238092 A1 | 8/2015 | Masumura |
| 2015/0241342 A1 | 8/2015 | Zhou |
| 2015/0346027 A1 | 12/2015 | Khare |
| 2015/0351635 A1 | 12/2015 | Cerussi |
| 2016/0085135 A1 | 3/2016 | Park |
| 2016/0157723 A1 | 6/2016 | Kanick |
| 2016/0262723 A1 | 9/2016 | Zhu |
| 2016/0363527 A1 | 12/2016 | Ruan |
| 2017/0118423 A1 | 4/2017 | Zhou |
| 2017/0163946 A1 | 6/2017 | Komanduri |
| 2017/0168565 A1 | 6/2017 | Cohen |
| 2017/0202633 A1 | 7/2017 | Liu |
| 2017/0230555 A1 | 8/2017 | Tabirian |
| 2017/0231501 A1 | 8/2017 | Culver |

OTHER PUBLICATIONS

Hofmann et al. Differential light detector, Rev. Sci. Instrum, Feb. 1979, vol. 50, No. 2, paes 249-252.
Freund et al. Memory Effects in Propagation of Ooptical Waves through Disordered Media, Physical Review Letters, Nov. 14, 1988, vol. 61, No. 20, pp. 2328-2331.
Goodman et al. Wavefront-Reconstruction Imaging Through Random Media, 15 Jun. 1966, vol. 8, No. 12, pp. 311-313.
Peng et al. Low loss liquid crystals for infrared applications, Liquid Crystal, 2014, vol. 41, No. 11, pp. 1545-1552.

* cited by examiner

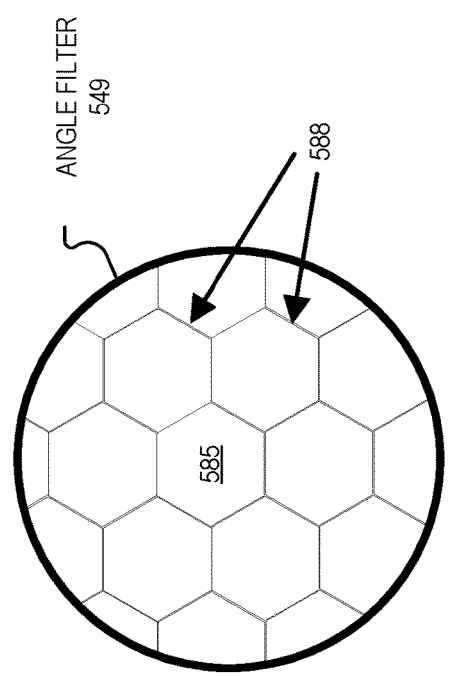
FIG. 5A
FIG. 5B

10,962,929 B2

INTERFERENCE OPTICS FOR OPTICAL IMAGING DEVICE

CROSS-REFERENCE TO RELATED APPLICATIONS

This application claims priority to U.S. provisional Application No. 62/731,308 filed Sep. 14, 2018, which is hereby incorporated by reference.

TECHNICAL FIELD

This application is related to optical imaging.

BACKGROUND INFORMATION

Imaging devices are used in contexts such as healthcare, navigation, and security, among others. Imaging systems often measure radio waves or light waves to facilitate imaging. Imaging that measures light scattered by an object is especially challenging and advances to the devices, systems, and methods to improve optical imaging are sought to increase speed, increase resolution, reduce size and/or reduce cost.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

FIGS. 5A-5B illustrate an example angle filter, in accordance with an embodiment of the disclosure.

DETAILED DESCRIPTION

Figure 1A:
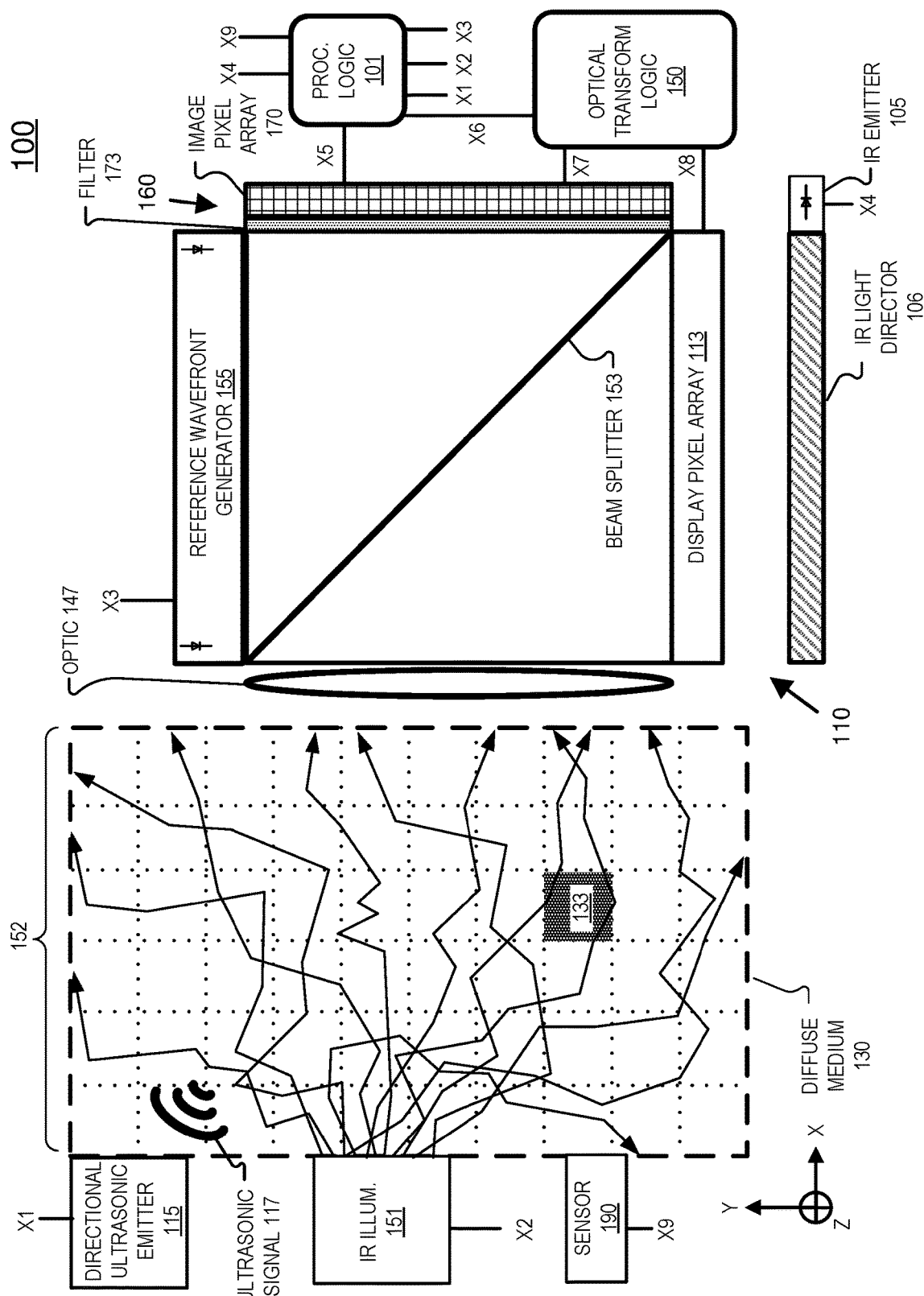
FIGS. 1A-1C illustrate an example imaging system that includes a display pixel array, an image pixel array, and a beam splitter, in accordance with an embodiment of the disclosure.

Embodiments of interference optics for an optical imaging device are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

This disclosure will generally describe imaging a diffuse medium in the context of human tissue in the medical context, however, the content of this disclosure may be applied to medical imaging, navigation, security, scientific research, or other contexts that image diffuse mediums or objects.

Human tissue is translucent to infrared light, although different parts of the human body (e.g. skin, blood, bone) exhibit different absorption coefficients. Researchers have attempted to use the properties of infrared light for medical imaging purposes, but size and cost constraints have been prohibitive for wide-scale adoption. Illuminating tissue and other diffuse mediums with near-infrared light for imaging purposes is sometimes referred to as Diffuse Optical Tomography. In one Diffuse Optical Tomography technique, time-of-flight (TOF) imaging can theoretically be employed by measuring the time it takes for "ballistic" photons (those photons that are not scattered) to pass through tissue. Since the ballistic photons reach the sensor the fastest, they are the least scattered (have the shortest optical path) and thus some conclusion can be drawn to create an image of the tissue that is illuminated by infrared light. However, TOF imaging generally requires specialty hardware (e.g. picosecond pulsed lasers and single photon detectors) to facilitate ultra-fast shutters on sensors that are able to image at the speed of light and the systems are overall very expensive and bulky. TOF imaging also requires an input of approximately 10-100 fold (or more) light intensity into the body than is received at the detector. Thus, efficacy and power limitations as well as safety limits on input intensity limit TOF imaging resolution, depth and utility.

In contrast to TOF imaging, some embodiments of this disclosure utilize a holographic imaging signal to direct infrared light to a voxel of a diffuse medium (e.g. a brain or tissue). A device or system of the disclosure may illuminate a diffuse medium with an infrared light while an ultrasound emitter is focused on a particular voxel. The infrared light encountering the particular voxel may be wavelength-shifted by the ultrasonic signal. The wavelength-shifted infrared imaging signal can be measured by a light detector (e.g. image pixel array). An optical transformation may be performed to generate a holographic pattern to be driven onto a display pixel array. When the display pixel array is illuminated by a light source having the same wavelength as the wavelength-shifted infrared imaging signal, (while the holographic pattern is driven onto the display pixel array), a reconstructed version of the received wavelength-shifted infrared imaging signal may be directed back to the voxel to focus on the voxel so that an exit signal generated by the voxel can be measured by a sensor. The exit signal is the infrared light of the holographic beam that is reflected from and/or transmitted through the voxel. By capturing images of the exit signal changes at a voxel or group of voxels (e.g. oxygen saturation in red blood cells, scattering changes induced by potential differences in an activated neuron, fluorescent contrast agents and other optical changes) in the diffuse medium, changes to that voxel or group of voxels can be recorded over time.

In an embodiment of the disclosure, a device or system illuminates a diffuse medium with an infrared light while an ultrasound emitter is focused on a particular voxel. The infrared light encountering the particular voxel may be wavelength-shifted by the ultrasonic signal. The wavelength-shifted infrared imaging signal can be measured by a light detector (e.g. image pixel array). Extraction logic may isolate the wavelength-shifted infrared imaging signal and extract intensity data and then populate a voxel value of a composite image with the intensity data. The composite image may include a three-dimensional image of the diffuse medium.

In an embodiment of the disclosure, interference optics generate an interference of a wavelength-shifted infrared exit signal and an infrared reference beam so that a sensor (e.g. image pixel array) can capture an interference image of the interference. These embodiments and others will be described in more detail with references to FIGS. 1A-7.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Throughout this specification, several terms of art are used. These terms are to take on their ordinary meaning in the art from which they come, unless specifically defined herein or the context of their use would clearly suggest otherwise.

Figure 1B:
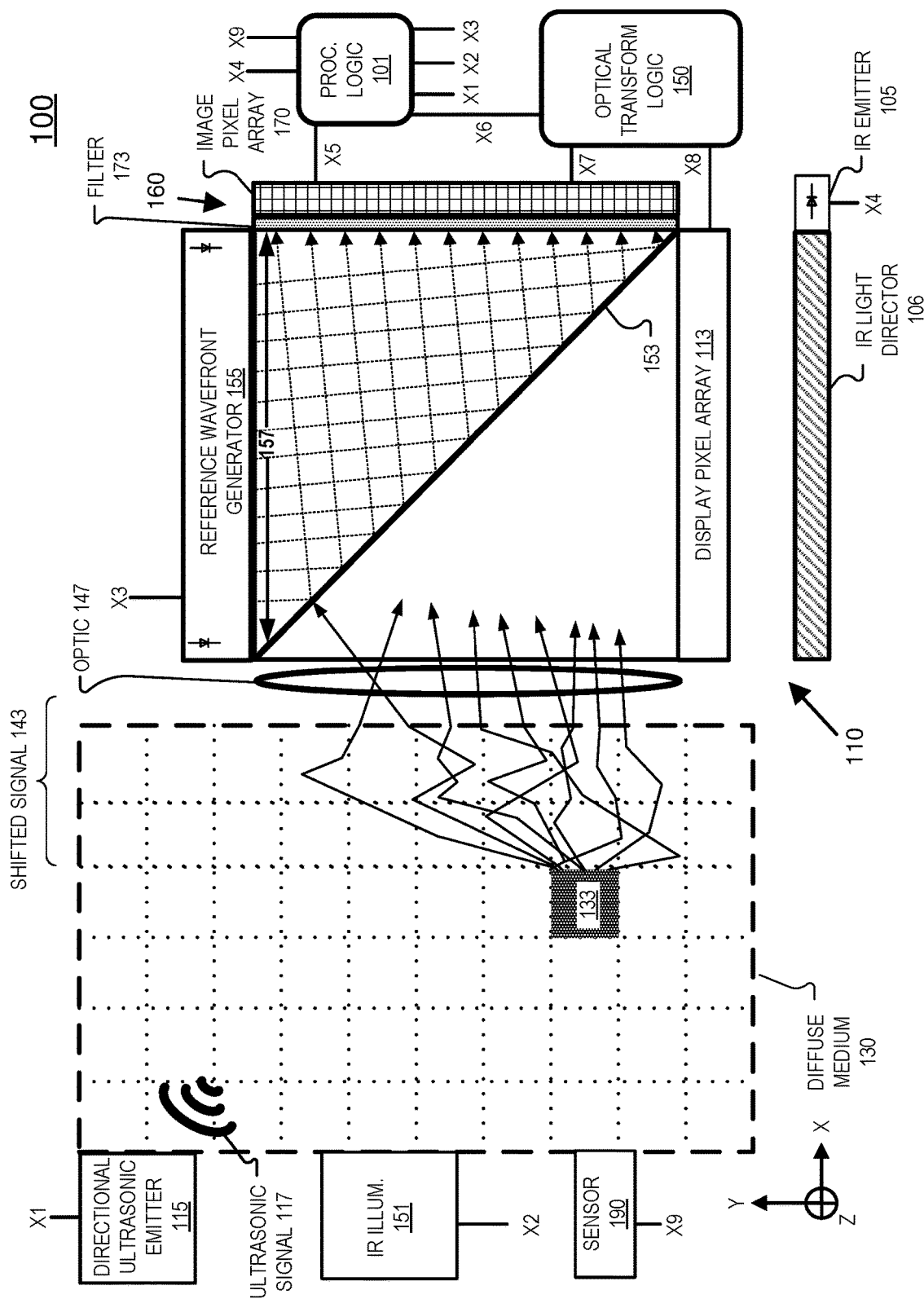
Figure 1C:
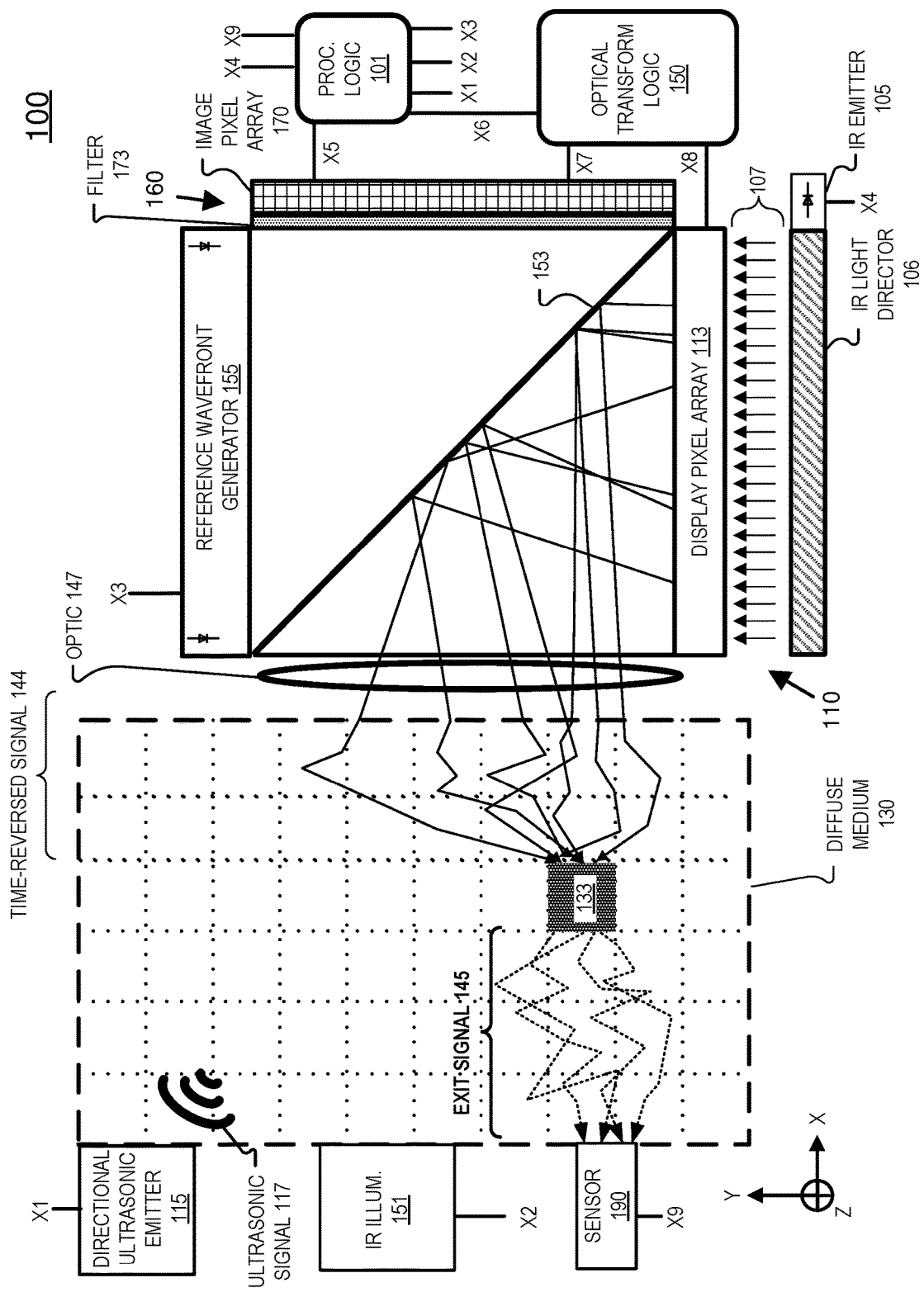

FIGS. 1A-1C illustrate an example imaging system that includes a display pixel array, an image pixel array, and a beam splitter, in accordance with an embodiment of the disclosure. In FIG. 1A, imaging system 100 includes processing logic 101, a spatial light modulator (SLM) 110, and image module 160. Imaging module 160 includes image pixel array 170 and filter(s) 173. In FIG. 1A, imaging system 100 also includes a directional ultrasonic emitter 115 coupled to be driven by processing logic 101. In FIG. 1A, SLM 110 includes an infrared emitter 105, an infrared light director 106, and a display pixel array 113. Display pixel array 113 may be an LCD (liquid crystal display), for example. The LCD display may be an active-matrix (using thin-film-transistors) or a passive matrix LCD. In one embodiment, the LCD display has pixels that are smaller than 7 microns. In other embodiments, SLM 110 may include a reflective architecture such as a liquid-crystal-on silicon (LCOS) display being illuminated by infrared light, for example. Other known transmissive and reflective display technologies may also be utilized as SLM 110. System 100 may include a plurality of discrete devices that incorporate components of system 100, in some embodiments.

Processing logic 101 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 101 to store instructions to execute operations and/or store data. A "memory" or "memories" described in this disclosure may include volatile or non-volatile memory architectures.

System 100 includes an infrared illuminator 151. Processing logic 101 is coupled to selectively activate IR illuminator 151 via output X2, in the illustrated embodiment. Infrared illuminator 151 may include an infrared laser generating a general illumination emission 152. Of course, an infrared laser may generate monochromatic coherent infrared light. Monochromatic light may be defined as light within a 4 nm frequency band, for example. The infrared light that IR illuminator 151 emits may be centered around a frequency in the 680-1000 nm range. In one embodiment, the infrared light that IR illuminator 151 emits may be centered around a frequency in the 1600-1700 nm range. In one example, IR illuminator 151 generates monochromatic light centered around 680 nm. In one example, IR illuminator 151 generates monochromatic light centered around 850 nm. The infrared illuminator 151 is disposed to direct the general illumination emission 152 into the diffuse medium 130. In the context of tissue, general illumination emission 152 will be significantly scattered within tissue within as little as 1 cm of depth into the tissue when tissue is the diffuse medium 130. At least a portion of the general illumination emission 152 will encounter voxel 133, as illustrated in FIG. 1A.

System 100 also includes an ultrasonic emitter 115. Ultrasonic emitter 115 is configured to focus an ultrasonic signal 117 to a point in three-dimensional space. In the medical context, the ultrasonic emitter 115 is configured to focus an ultrasonic signal 117 to a voxel within the human body. The voxel may be within the brain, abdomen, or uterus, for example. Processing logic 101 is coupled to drive directional ultrasonic emitter 115 to focus ultrasonic signal 117 to different locations in three-dimensional space via output X1, in the illustrated embodiment. The directional ultrasonic emitter 115 can be driven to focus an ultrasonic signal to voxel 133 in three-dimensional diffuse medium 130, for example. Focusing an ultrasonic signal 117 to a given voxel of tissue (e.g. voxel 133) influences the portion of illumination emission 152 that encounters the voxel by wavelength-shifting that portion of illumination emission 152 that propagates through that voxel.

In FIG. 1B, the wavelength-shifted portion of the general illumination emission 152 is illustrated as shifted infrared imaging signal 143. Being influenced by ultrasonic signal 117, shifted signal 143 has a different wavelength (hereinafter referred to as lambda-two) than general illumination emission 152 (referred to as lambda-one). In some embodiments, the delta between lambda-one and lambda-two may be less than 1 nanometer. In an embodiment, the delta between lambda-one and lambda-two may be less than 20 femtometer.

System 100 receives (at least a portion of) shifted infrared imaging signal 143. An input optic 147 may optionally be included in system 100. Input optic 147 may receive shifted signal 143 and direct the shifted signal 143 to be incident on image pixel array 170. In one embodiment, input optic 147 is configured to filter out an angled portion of the shifted signal 143. In one embodiment, the angled portion of the shifted signal 143 has a plus-or-minus angle of incidence upon the input optic 147 that is higher than an angle threshold. In one embodiment, the sine of twice the angle threshold is approximately equivalent to a wavelength of the shifted signal 143 (lambda-two) divided by twice a distance between two pixels of the image pixel array 170. In one embodiment, the angle threshold is between five and seven degrees.

Still referring to FIG. 1B, reference wavefront generator 155 generates an infrared reference wavefront 157 having the lambda-two wavelength so that infrared reference wavefront 157 interferes with the incoming shifted signal 143. Reference wavefront generator 155 may include one or more laser diodes and corresponding optics to generate a substantially uniform wavefront. Processing logic 101 is coupled to selectively activate reference wavefront generator 155 via output X3, in the illustrated embodiment.

A first portion of the infrared reference wavefront 157 is redirected to the image pixel array 170 by beam splitter 153 while a second remaining portion of wavefront 157 passes through beam splitter 153. Shifted signal 143 encounters beam splitter 153 and a first portion of the shifted signal 143 passes through beam splitter 153 while the remaining second portion of the shifted signal 143 is reflected by beam splitter 153. The first portion of the shifted signal 143 that passes through beam splitter 153 interferes with the first portion of wavefront 157 that is redirected to image pixel array 170 and image pixel array 170 captures an infrared image of the interference between shifted signal 143 and infrared reference wavefront 157.

In one embodiment, reference wavefront generator 155 is disposed to deliver the infrared reference wavefront 157 to the image pixel array 170 at an angle to a pixel plane of the image pixel array 170. Image pixel array 170 may include image pixels disposed in a two-dimensional rows and columns that define the pixel plane of the image pixel array 170. In one embodiment, the angle is between five and seven degrees so that the infrared reference wavefront 157 encounters the image pixels of image pixel array 170 at a non-orthogonal angle. Angling the infrared reference wavefront 157 may change the interference orientation and size between shifted signal 143 and wavefront 157, which may enable better signal isolation at the image pixel array 170. Processing logic 101 is coupled to initiate the image capture by image pixel array 170 via output X5, in the illustrated embodiment.

A linear polarizer may be included in system 100 to polarize shifted signal 143 to have the same polarization orientation as infrared reference wavefront 157. The light source of reference wavefront generator 155 may generate linear polarized light which imparts a polarization orientation to infrared reference wavefront 157. The linear polarizer may be included in optic 147, filter 173, or in a linear polarizer disposed between optic 147 and filter 173, in FIG. 1.

In the illustrated embodiment, an infrared filter 173 is disposed between beam splitter 153 and image pixel array 170. Infrared filter 173 may pass the wavelength of infrared light emitted by reference wavefront generator 155 (lamda-two) and reject ambient light in a bandpass that is 10 nm or greater.

Image pixel array 170 may be implemented with an a-Si (amorphous Silicon) thin film transistors, in some embodiments or a CMOS (Complimentary Metal-Oxide-Semiconductor) image sensor, in some embodiments. Image pixel array 170 can be a commercially available image sensor. In one embodiment, image pixel array 170 has image pixels having a pixel pitch of 3.45 microns. In one embodiment, image pixel array 170 has image pixels having a pixel pitch of 1.67 microns. The pixel resolution of image pixel array 170 may vary depending on the application. In one embodiment, the image pixel array 170 is 1920 pixels by 1080 pixels. In one embodiment, the image pixel array is 40 Megapixels or more. Image pixel array 170 can capture an infrared image of an interference between shifted signal 143 and IR reference wavefront 157 by measuring the image charge generated in each pixel during a given integration period that is determined by an electronic shutter. The electronic shutter may be a global shutter (where each pixel measures the incident light during a same time period) or a rolling shutter. The electronic shutter can be actuated by processing logic 101 via input/output X5. Input/output X5 may include digital input/output lines as well as a data bus. Image pixel array 170 is communicatively coupled to optical transform logic 150 to send the captured infrared image(s) to optical transform logic 150 for further processing. In some embodiments, the integration period of the pixels of the image pixel array 170 is determined by the length of a laser pulse. Image pixel array 170 may include a local (on-board) digital signal processor (DSP), in some embodiments, and optical transform logic 150 may receive the captured infrared images from the DSP.

Optical transform logic 150 is coupled to image pixel array 170 via communication channel X7, in the illustrated embodiment. Optical transform logic is also communicatively coupled to processing logic 101 via communication channel X6. Optical transform logic 150 is coupled to receive the captured infrared image from the image pixel array and provide a holographic pattern to be driven onto the display pixel array 113. The optical transform logic 150 is configured to extract phase data of the interference captured by the infrared image and the holographic pattern is generated from the phase data. A more detailed description of example optical transform logic is described in U.S. patent application Ser. No. 15/942,480, which is hereby incorporated by reference.

Referring now to FIG. 1C, display pixel array 113 is configured to generate an infrared holographic imaging signal 144 (reconstruction of signal 143) according to a holographic pattern driven onto the array 113. Optical transform logic 150 is coupled to provide the array 113 the holographic pattern via communication channel X8.

In FIG. 1C, display pixel array 113 is illustrated as a transmissive LCD that is illuminated by infrared wavefront 107. In the illustrated embodiment, infrared (IR) emitter 105 is coupled to be driven by output X4 of processing logic 101. When processing logic 101 turns on (activates) IR emitter 105, infrared light propagates into IR light director 106. IR light director 106 may be a light guide plate similar to those found in conventional edge lit LCDs. IR light director 106 may be a slim prism utilizing TIR (total internal reflection). IR light director 106 redirects the infrared light toward display pixel array 113. IR light director 106 may include a sawtooth grating to redirect the infrared light toward array 113. IR emitter 105 is an infrared laser diode that emits monochromatic infrared light, in one embodiment.

Steerable infrared beams can be generated by SLM 110 by driving different holographic patterns onto display pixel array 113. Each different holographic pattern can steer (focus) the infrared light in a different direction. The directional nature of the infrared beam is influenced by the constructive and destructive interference of the infrared light emitted from the pixels of SLM 110. As an example, a holographic pattern that includes different "slits" at different locations can generate different infrared beams. The "slits" can be generated by driving all the pixels in the display pixel array 113 to "black" (not transmissive) except for the pixels where the "slits" are located are driven to be "white" (transmissive) to let the infrared light propagate through. The pixel size of display pixel array 113 may be 1 micron, although in some embodiments pixels sized up to 10 times the wavelength of the infrared light can be used. In one example, if IR emitter 105 is an 850 nm laser diode, the pixel size of SLM 110 may be 850 nm. The pixel size influences the angular spread of a hologram since the angular spread is given by the Grating Equation:

$$\sin(\theta) = m\lambda/d \quad \text{(Equation 1)}$$

where θ is the angular spread of light, m is an integer number and the order of diffraction, and d is the distance of two pixels (a period). Hence, smaller pixel size generally yields more design freedom for generating holographic beams, although pixels sizes that are greater than the wavelength of light can also be used to generate holographic imaging signals. Display pixel array 113 may include square pixels (rather than the rectangular pixels in conventional RGB LCDs) so that the Grating Equation is applicable in both the row dimension and column dimension of the display pixel array 113.

In the illustrated embodiment, processing logic 101 selectively activates infrared emitter 105 and infrared light director 106 directs the infrared light to illuminate display pixel array 113 as infrared wavefront 107 while the holographic pattern is driven onto array 113. Infrared wavefront 107 is the same wavelength as infrared reference wavefront 157. Processing logic 101 may deactivate reference wavefront generator 155 while display pixel array 113 is being illuminated by infrared wavefront 107. Processing logic 101 may be configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Display pixel array 113 generates an infrared holographic imaging signal when the holographic pattern is illuminated by infrared wavefront 107 and the infrared holographic imaging signal is redirected by beam splitter 153 to exit system 100 as a reconstruction 144 (in reverse) of the shifted signal 143 that entered system 100. Reconstructed signal 144 follows (in reverse) whatever scattered path that shifted signal 143 took from voxel 133 to beam splitter 153 so reconstructed signal 144 is essentially "focused" back onto voxel 133.

Voxel 133 may absorb or scatter reconstructed signal 144 according to biological and/or optical characteristics of voxel 133 and sensors may measure an exit signal 145 of the reconstructed signal 144 that encounters voxel 133. System 100 may optionally include a sensor 190 coupled to processing logic 101 via an input/output X9 to initiate light measurement of exit signal 145 and pass the light measurement to processing logic 101. Although exit signal 145 is illustrated as being directed to sensor 190, the illustrated exit signal 145 is only a portion of the exit signal 145 that will be generated from signal 144 encountering voxel 133 and exit signal 145 will have many exit points from diffuse medium in addition to the illustrated portion of exit signal 145. The sensors that measure this exit signal may simply measure the amplitude of the exit signal. Sensor 190 may be a photodiode or a CMOS image sensor, for example. In one embodiment, the image pixel array 170 is used to measure the amplitude and/or phase of exit signal 145. The amplitude and/or phase of the exit signal 145 may be used to generate an image of diffuse medium 130. A reconstructed signal 144 may be directed to voxel 133 multiple times (with multiple corresponding measurements of exit signal 145) so that biological changes in voxel 133 may be recorded over a time range.

System 100 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array gives display pixel array 113 the ability to generate steerable holographic infrared beams that can focus an infrared signal (e.g. 144) to different voxels in three-dimensional space to facilitate the raster scanning of diffuse medium 130.

In one embodiment, processing logic 101 is configured to drive the reference wavefront generator 155 to emit the infrared reference wavefront 157 and initiate the infrared image capture by the image pixel array 170 while the reference wavefront generator 155 and the infrared illuminator 151 are emitting the infrared reference wavefront 157 and the general illumination emission 152, respectively.

Figure 2A:
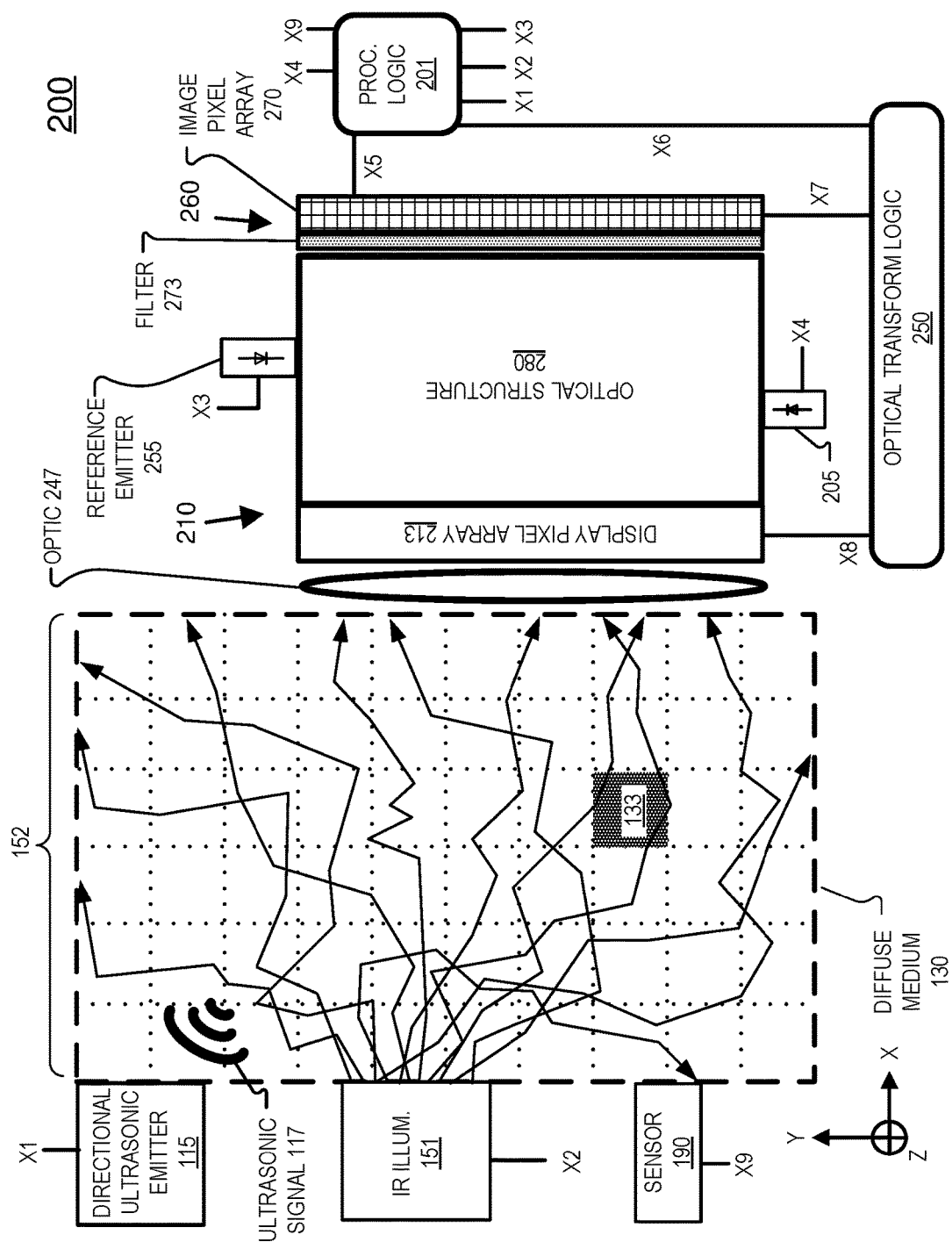
FIGS. 2A-2C illustrate an example imaging system that includes an image pixel array receiving an exit signal through a display pixel array, in accordance with an embodiment of the disclosure.
Figure 2B:
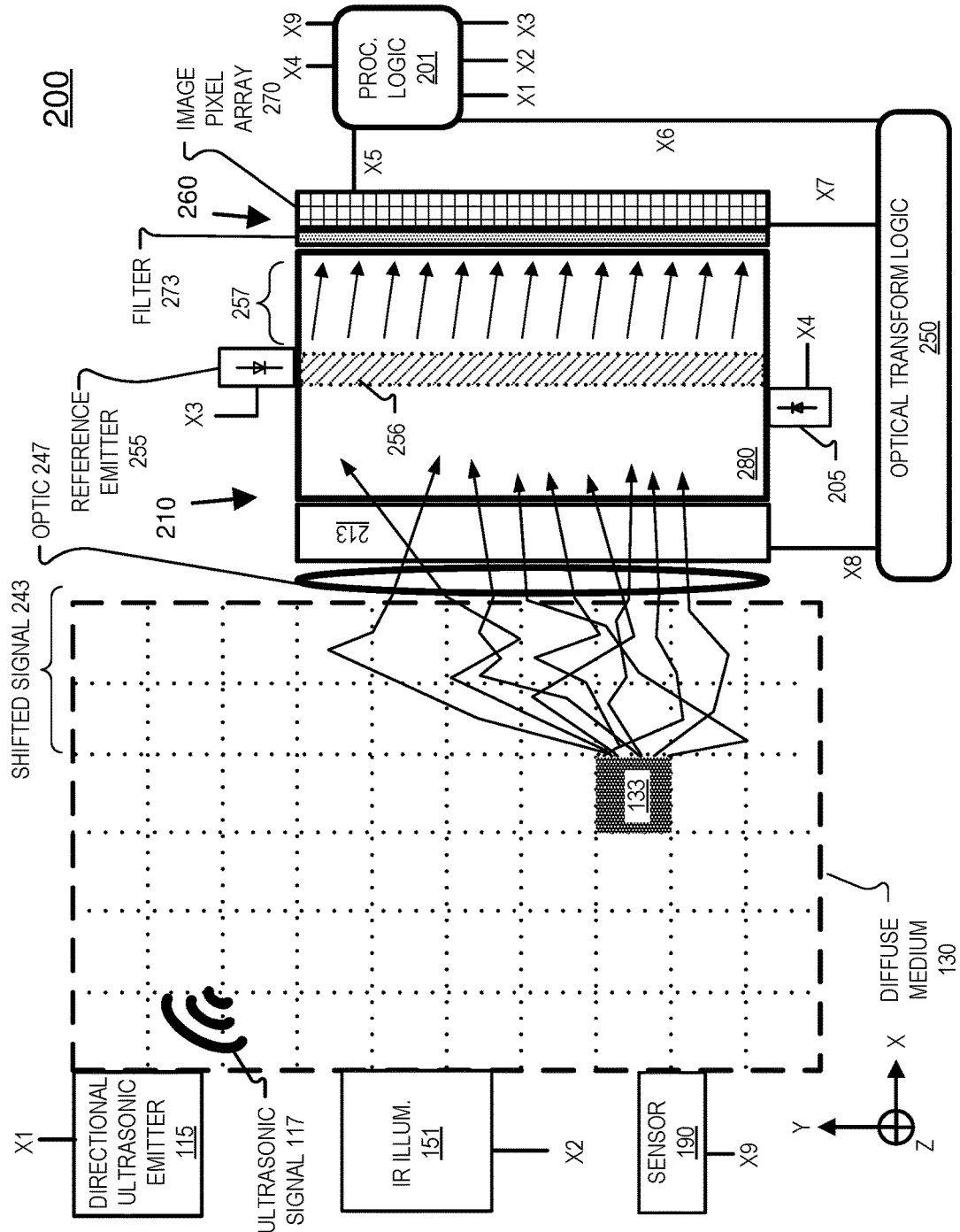
Figure 2C:
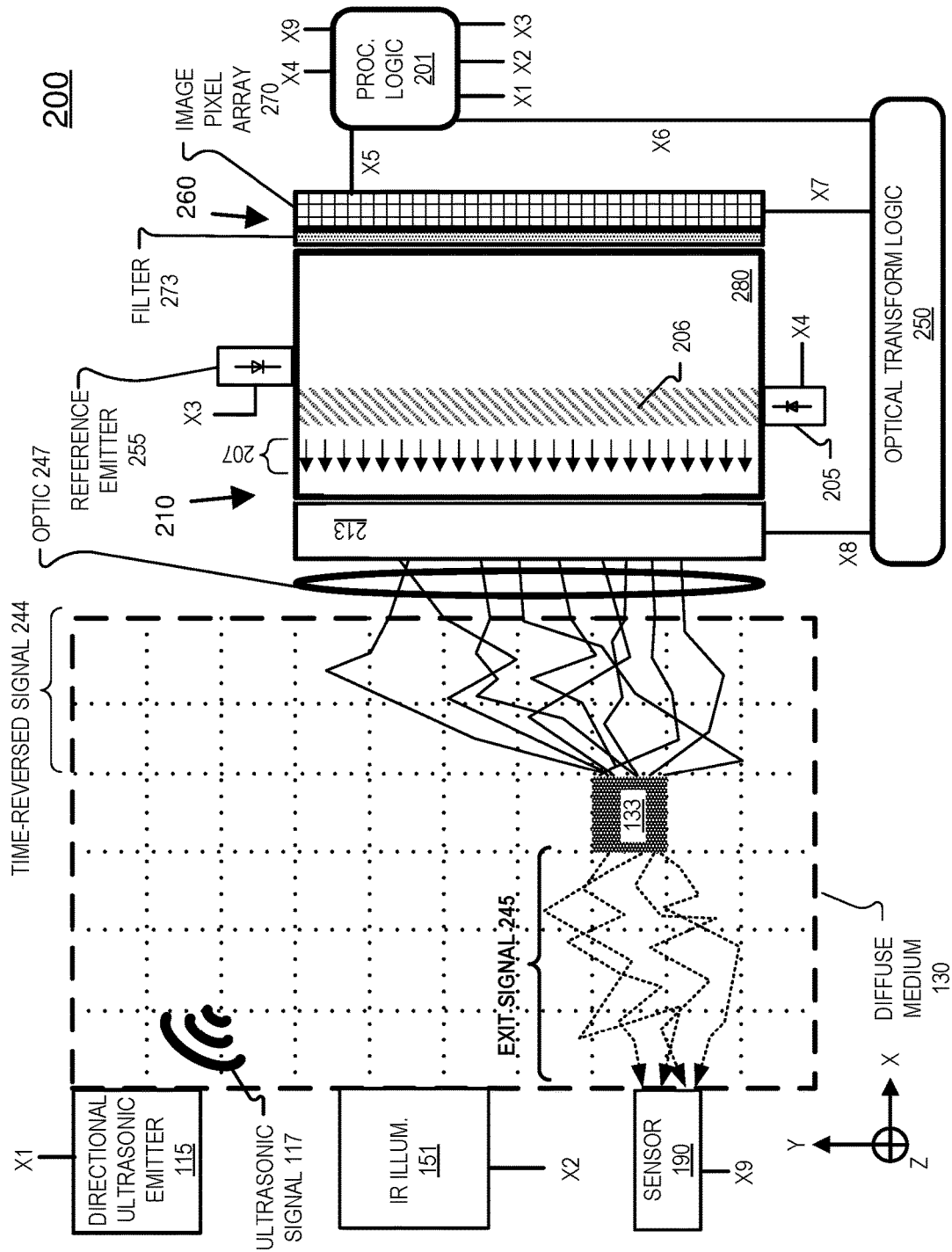

FIGS. 2A-2C illustrate an example imaging system 200 that includes an optical structure disposed between a display pixel array and an image pixel array, in accordance with an embodiment of the disclosure. System 200 illustrated in FIGS. 2A-2C functions similarly to system 100 of FIGS. 1A-1C although there are differences associated with the different positioning of the SLM 210, the imaging module 260, and the addition of optical structure 280.

Similarly to FIG. 1A, in FIG. 2A, processing logic 201 is coupled to drive directional ultrasonic emitter 115 to focus ultrasonic signal 117 to different locations in three-dimensional space, via output X1. Processing logic 201 is also coupled to selectively activate IR illuminator 151 via output X2, in the illustrated embodiment. System 200 may include a plurality of discrete devices that incorporate components of system 200, in some embodiments.

Imaging module 260 includes image pixel array 270 and filter(s) 273. In FIG. 2A, imaging system 200 also includes a directional ultrasonic emitter 115 coupled to be driven by processing logic 201. SLM 210 includes an infrared emitter 205, an infrared light director 206 (illustrated in FIG. 2C), and a display pixel array 213. Display pixel array 213 is a transmissive pixel array, in FIG. 2A.

Processing logic 201 may include a processor, microprocessor, cluster of processing cores, FPGA (field programmable gate array), and/or other suitable combination of logic hardware. In some embodiments, memories (not illustrated) are integrated into the processing logic to store instructions to execute operations and/or store data. An external memory or memories (not illustrated) may also be coupled to processing logic 201 to store instructions to execute operations and/or store data. A "memory" or "memories" described in this disclosure may include volatile or non-volatile memory architectures.

With ultrasonic signal 117 focused on voxel 133 in diffuse medium 130, IR illuminator 151 is selectively activated to emit general illumination emission 152 and a portion of emission 152 encounters voxel 133.

In FIG. 2B, the wavelength-shifted portion of the general illumination emission 152 is illustrated as shifted infrared imaging signal 243. Being influenced by ultrasonic signal 117, shifted infrared imaging signal 243 has a different wavelength (lambda-two) than general illumination emission 152 (lambda-one).

System 200 receives (at least a portion of) shifted signal 243. An input optic 247 may optionally be included in system 200. Input optic 247 may receive shifted signal 243 and focus the shifted signal 243 to be incident on image pixel array 270. In one embodiment, input optic 247 is configured to filter out an angled portion of the shifted signal 243, as described with regard to an embodiment of input optic 147.

Still referring to FIG. 2B, reference emitter 255 is configured to selectively emit an infrared reference light having the lambda-two wavelength so that infrared reference wavefront 257 interferes with the incoming shifted signal 243. Reference emitter 255 may include one or more laser diodes and reference director optic 256 in optical structure 280 may direct the lambda-two infrared reference light to image pixel array 270 as a substantially uniform infrared reference wavefront 257. Processing logic 201 is coupled to selectively activate reference emitter 255 via output X3, in the illustrated embodiment.

A linear polarizer may be included in system 200 to polarize shifted signal 243 to have the same polarization orientation as infrared reference wavefront 257. Reference emitter 255 may generate linear polarized light which imparts a polarization orientation to infrared reference wavefront 257. The linear polarizer may be included in optic 247, filter 273, or optical structure 280.

Shifted signal 243 may encounter input optic 247, display pixel array 213, and optical structure 280 prior to becoming incident upon image pixel array 270. The shifted signal 243 interferes with infrared reference wavefront 257 and image pixel array 270 captures an infrared image of the interference between shifted signal 243 and infrared reference wavefront 257. To allow shifted signal 243 to pass through display pixel array 213, each of the display pixels of the display pixel array 213 may be driven to a transmissive state while IR illuminator 151 and reference emitter 255 are activated.

In one embodiment, reference director optic 256 is configured to deliver the infrared reference wavefront 257 to the image pixel array 270 at an angle to a pixel plane of the image pixel array 270. Processing logic 201 is coupled to initiate the image capture by image pixel array 270 via output X5, in the illustrated embodiment.

In the illustrated embodiment, an infrared filter 273 is disposed between optical structure 280 and image pixel array 270. Infrared filter 273 may include the same configuration as infrared filter 173. Image pixel array 270 may include the same configuration as image pixel array 170. Image pixel array 270 is communicatively coupled to optical transform logic 250 to send the captured infrared image(s) to optical transform logic 250 for further processing. Optical transform logic 250 is coupled to image pixel array 270 via communication channel X7, in the illustrated embodiment. Optical transform logic 250 is coupled to receive the captured infrared image from the image pixel array 270 and provide a holographic pattern to be driven onto the display pixel array 213. The optical transform logic 250 is configured to extract phase data of the interference captured by the infrared image and the holographic pattern is generated from the phase data.

Referring now to FIG. 2C, display pixel array 213 is configured to generate an infrared holographic imaging signal 244 according to a holographic pattern driven onto the array 213. Optical transform logic 250 is coupled to provide the array 213 the holographic pattern to array 213 via communication channel X8.

In FIG. 2C, display pixel array 213 is illustrated as a transmissive LCD that is illuminated by infrared wavefront 207. In the illustrated embodiment, infrared emitter 205 is coupled to be driven by output X4 of processing logic 201. When processing logic 201 turns on (activates) IR emitter 205, infrared light propagates into IR light director 206. IR light director 206 redirects the infrared light toward display pixel array 213. IR emitter 205 is an infrared laser diode that emits monochromatic infrared light, in one embodiment.

In the illustrated embodiment, processing logic 201 selectively activates infrared emitter 205 and infrared light director 206 directs the infrared light to illuminate display pixel array 213 as infrared wavefront 207 while the holographic pattern is driven onto array 213. Infrared wavefront 207 is the same wavelength as infrared reference wavefront 257. Processing logic 201 may deactivate reference emitter 255 while display pixel array 213 is being illuminated by infrared wavefront 207. Processing logic 201 may be configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

Display pixel array 213 generates an infrared holographic imaging signal 244 when the holographic pattern is illuminated by infrared wavefront 207 and the infrared holographic imaging signal 244 exits system 200 as a reconstruction (in reverse) of the shifted signal 243 that entered system 200. Reconstructed signal 244 follows (in reverse) whatever scattered path that shifted signal 243 took from voxel 133 to the display pixel array 213 so reconstructed signal 244 is essentially "focused" back onto voxel 133.

Voxel 133 may absorb or scatter reconstructed signal 244 according to biological characteristics of voxel 133 and sensors may measure an exit signal 245 of the reconstructed signal 244 that encounters voxel 133. System 200 may optionally include a sensor 190 coupled to processing logic 201 via an input/output X9 to initiate light measurement of exit signal 245 and pass the light measurement to processing logic 201. Although exit signal 245 is illustrated as being directed to sensor 190, the illustrated exit signal 245 is only a portion of the exit signal 245 that will be generated from signal 244 encountering voxel 133 and exit signal 245 will have many exit points from diffuse medium in addition to the illustrated portion of exit signal 245. The sensors that measure this exit signal may simply measure the amplitude of the exit signal. In one embodiment, the image pixel array 270 is used to measure the amplitude and/or phase of exit signal 245. The amplitude and/or phase of the exit signal 245 may be used to generate an image of diffuse medium 130. A reconstructed signal 244 may be directed to voxel 133 multiple times (with multiple corresponding measurements of exit signal 245) so that biological changes in voxel 133 may be recorded over a time range.

System 200 may refocus directional ultrasonic emitter 115 to different voxels of diffuse medium 130 and repeat the processes disclosed herein to raster scan diffuse medium 130 in order to generate a three-dimensional image of diffuse medium 130. Driving different holographic patterns onto display pixel array 213 gives display pixel array 213 the ability to generate steerable holographic infrared beams that can focus the reconstructed signal (e.g. 244) to different voxels in three-dimensional space to facilitate the raster scanning of diffuse medium 130.

In one embodiment, processing logic 201 is configured to drive the reference emitter 255 to emit the infrared reference wavefront 257 and initiate the infrared image capture by the image pixel array 270 while the reference emitter 255 and the infrared illuminator 151 are emitting the infrared reference wavefront 257 and the general illumination emission 152, respectively.

In system 200, image pixel array 270 is disposed in a parallel plane to display pixel array 213. However, in some embodiments, image pixel array 270 may be angled to increase the signal of interference between the infrared reference wavefront 257 and shifted signal 243. In system 100, image pixel array 170 is illustrated as being in a plane that is orthogonal to display pixel array 113. However, in some embodiments, image pixel array 170 may be angled to increase the signal of interference between the infrared reference wavefront 157 and shifted signal 143.

Although not specifically illustrated in FIGS. 1A-2C, infrared illuminator 151, reference wavefront generator 155 and infrared emitter 105 may be fiber optic outputs that are provided light via fiber optic from a single laser source. Similarly, infrared illuminator 151, reference emitter 255, and infrared emitter 205 may be provided light via fiber optic from a single laser source. The light from the single laser source may be modulated (e.g. by an acoustic optical modulator) to direct the laser light to the proper fiber optic for illumination. A micro-electro-mechanical system (MEMS) mirror, a digital micromirror device (DMD), or a mirror galvanometer may be used to selectively couple light from a single source into different fiber optic paths, in different embodiments. The light from the single laser source may also be selectively wavelength-shifted (e.g. by an acoustic optical modulator) to provide IR illuminator 151 with lambda-one wavelength light and to provide reference elements 105, 205, 155, and 255 with lambda-two wavelength light.

Figure 3:
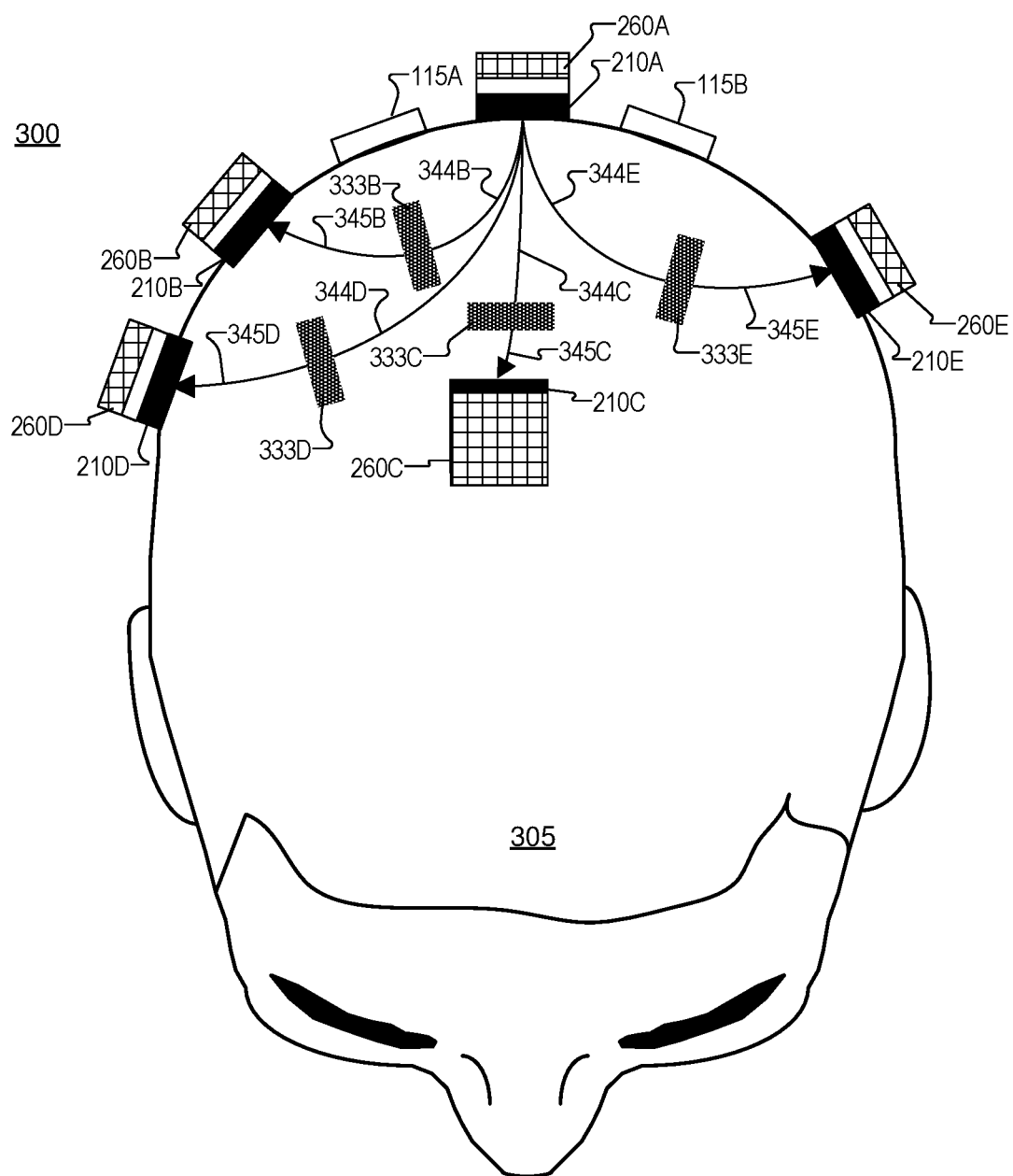
FIG. 3 illustrates an example placement of components of an imaging system in relationship to a human head, in accordance with an embodiment of the disclosure.

FIG. 3 illustrates an example placement of components of an imaging system 300 in relationship to a human head, in accordance with an embodiment of the disclosure. FIG. 3 is a top-down view of a human head 305. Imaging system 300 includes SLMs 210A-210E and imaging modules 260A-260E arranged as in system 200, and directional ultrasonic emitters 115A and 115B. Of course, SLMs 110 and imaging modules 160 may also be used instead of SLMs 210 and imaging modules 260 in imaging system 300. FIG. 3 shows that SLM 210A may generate multiple reconstructed infrared signals 344 that are directed to image different voxels 333 of the brain while the exit signals 345 are imaged by different imaging modules 260. The other SLMs 210B-210E may also generate reconstructed infrared signals 344 (not illustrated) directed to voxels where the exit signals are imaged by each of imaging modules 260A-E. Scientific literature suggests that the penetration depth of infrared light into tissue is around 10 cm so multiple SLMs 210 and imaging modules 160 may be needed to image the entire brain or other tissue. Although not illustrated, sensors 190 may also be placed around a diffuse medium such as human head 305 to measure the exit signals 345. A wearable hat may include system 300 so that system 300 can be worn as a wearable, in some embodiments. Other wearables may also include all or part of system 300.

Figure 4:
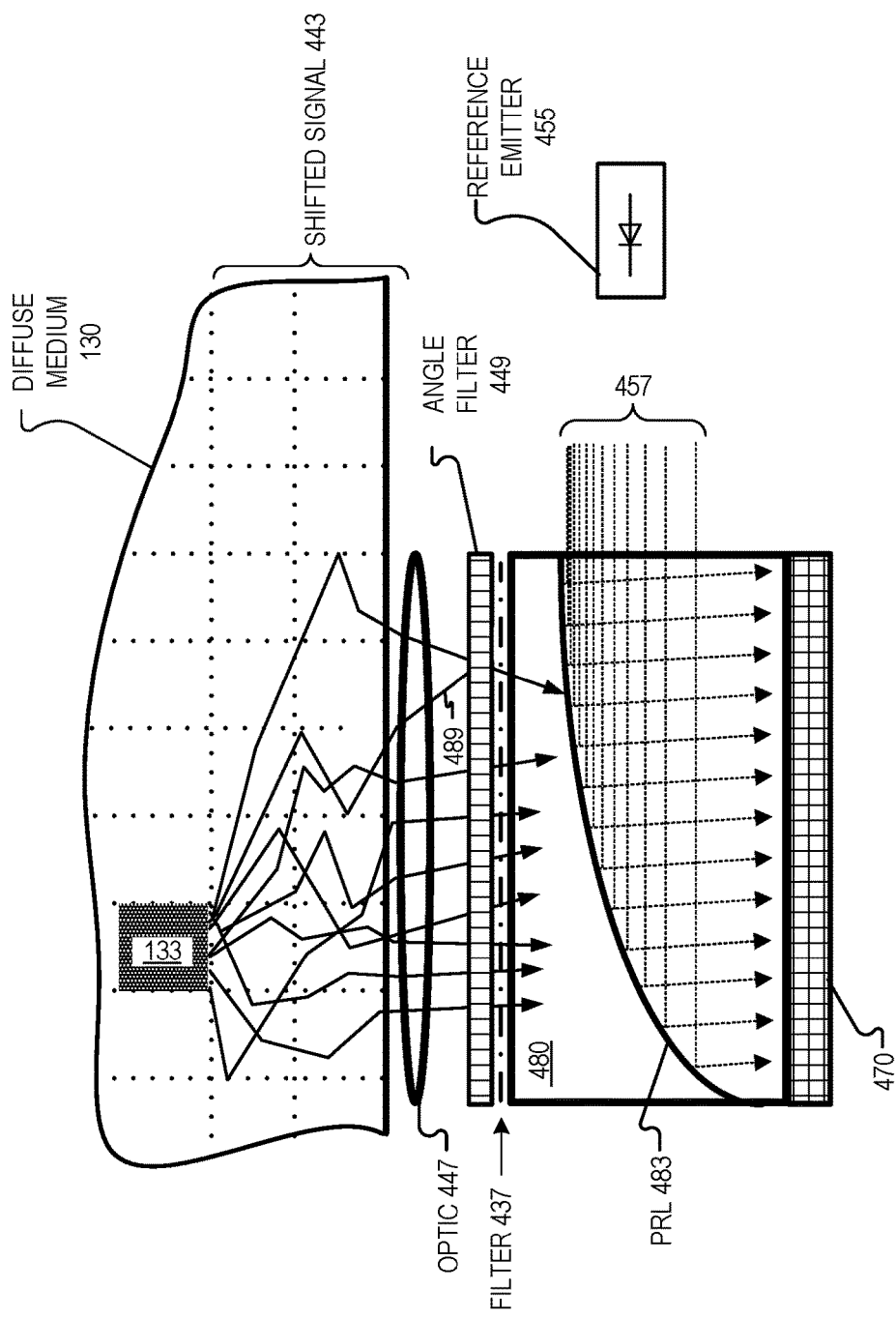
FIG. 4 illustrates an example imaging device having a partially reflective layer for directing an infrared reference beam, in accordance with an embodiment of the disclosure.

FIG. 4 illustrates an example imaging device 400 that includes example interference optics, in accordance with an embodiment of the disclosure. Device 400 includes a sensor 470, optical structure 480, and infrared reference emitter 455. Sensor 470 may include a two-dimensional image pixel array arranged in rows and columns that define a pixel plane of the sensor 470. Sensor 470 may be a CMOS image sensor in some embodiments. Optical structure 480 includes a partially reflective layer 483 disposed on a two-dimensional curvature. The curvature may be parabolic. In one embodiment, the curvature is an offset parabola configured to collimate a received infrared reference beam 457 and direct rays from infrared reference beam 457 to sensor 470 at an angle relative to a vector that is normal to a pixel plane of the sensor 470. In some embodiments the angle is between 4 and 8 degrees. In one embodiment, the angle is between 5 and 7 degrees.

Angle filter 449 may optionally be included in device 400 to pass rays of wavelength-shifted exit signal 443 that are within an angle of incidence range and reject rays of wavelength-shifted exit signal 443 that are outside the angle of incidence range. Angle filter 449 may be disposed on a filtering plane that is parallel to a pixel plan of the sensor. In one embodiment, incident rays that are greater than 10 degrees offset from a vector that is normal to the filtering plane are outside of the angle of incidence range. In one embodiment, incident rays that are greater than 5 degrees offset from a vector that is normal to the filtering plane are outside of the angle of incidence range. Partially reflective layer 483 is disposed between sensor 470 and the angle filter 449. Constraining the incident angle of wavelength-shifted exit signal 443 may assist in allowing in light that contributes to resolvable interference patterns generated by the interference of infrared reference beam 457 with signal 443.

In FIG. 4, device 400 includes an infrared filtering layer 437. Infrared filtering layer 437 may be a bandpass filter that is configured to pass an infrared wavelength band of the wavelength-shifted exit signal 443 and reject ambient light. In an embodiment, the wavelength band (the passband) is less than 2 nm. In an embodiment, the wavelength band (the passband) is less than 1 nm. The bandpass filter may have a 1 nm bandpass centered around a wavelength of wavelength-shifted exit signal 443 and be approximately 1 mm thick. By using infrared filtering layer 437 to block out light besides the wavelength of wavelength-shifted exit signal 443, an interference image captured by sensor 470 may be limited to the interference between the wavelength-shifted exit signal 443 and the infrared reference beam 457. Infrared filtering layer 437 may include a plurality of dielectric layers with thicknesses designed to be a dichroic bandpass filter, for example.

Infrared filtering layer 437 may be disposed on a filtering plane that is parallel to the pixel plane of sensor 470. Partially reflective layer 483 is disposed between infrared filtering layer 437 and sensor 470. In the illustrated embodiment, infrared filtering layer 437 is illustrated as outside of optical structure 480. In some embodiments, infrared filtering layer 437 may be included in optical structure 480. In one embodiment, optical structure 480 includes an optically transparent material to support partially reflective layer 483 and the curvature that partially reflective layer is disposed on and the infrared filtering layer 437 may be immersed in that same refractive material.

Infrared filtering layer 437 may be configured as an angle-selective infrared filtering layer that is configured to transmit rays of the wavelength-shifted exit signal 443 within an angle of incidence range and reject the rays of the wavelength-shifted exit signal that are outside of the angle of incidence range. Infrared filtering layer 437 may be disposed on a filtering plane that is parallel to a pixel plan of the sensor. In one embodiment, incident rays that are greater than 10 degrees offset from a vector that is normal to the filtering plane are outside of the angle of incidence range. In one embodiment, incident rays that are greater than 5 degrees offset from a vector that is normal to the filtering plane are outside of the angle of incidence range. The angle selection of infrared filtering layer 437 may be configured to pass rays of exit signal 443 that will become incident on sensor 470 while rejecting rays of exit signal 443 that have more extreme angles that would not become incident on sensor 470 due to the ray's greater angle of incidence with respect to the filtering plane. Furthermore, the size of interference fringes and separation of the interference fringes in the interference pattern decreases as the interference angle increases. As a thickness of the interference fringes approaches the pixel size of an image sensor capturing the interference pattern, resolving the interference fringes becomes more difficult. Thus, blocking the more extreme angles of exit signal 443 may increase the size of the interference fringes to assist in resolving the interference fringes. When infrared filtering layer 437 is also an angle-selective infrared filtering layer, angle filter 449 may not necessarily be utilized in the device since infrared filtering layer 437 is performing the angle selectivity function.

In operation, reference emitter 455 emits an infrared reference beam 457 that is the same wavelength as wavelength-shifted exit signal 443. Reference emitter 455 may be a coherent infrared illumination source (e.g. a laser) that provides the infrared reference beam to optical structure 480 by way of a fiber optic. Infrared reference beam 457 encounters partially reflective layer (PRL) 483. PRL 483 may be a 50/50 reflective layer that passes 50% of light and reflects 50% of light. In some embodiments, PRL 483 is less than 30% reflective. PRL 483 may be a partially reflective layer that passes 80% of light and reflects 20% of light. PRL 483 may be a partially reflective layer that passes 90% of light and reflects 10% of light. PRL 483 may be a partially reflective layer that passes 95% of light and reflects 5% of light. PRL 483 is configured to redirect beam 457 to sensor 470. PRL 483 may be disposed on a two-dimensional parabolic curvature configured to collimate beam 457 and direct the rays of beam 457 to sensor 470 at an angle (e.g. 5-7 degrees). Shifted signal 443 also encounters PRL 483 and a portion of signal 443 passes through PRL 483 toward image pixel array 470. The portion of signal 443 that passes through PRL 483 interferes with beam 457 and image pixel array 470 captures an interference image of an interference between signal 443 and 457. Additional optics (not illustrated) may be disposed between optical structure 480 and infrared reference emitter 455 to spread infrared reference beam 457 to properly encounter partially reflective layer 483.

Optic 447 may optionally be included in device 400 and be configured similar to optic 147. Angle filter 449 may optionally be included to provide a filter selecting for angles of signal 443 that are passed. In FIG. 4, most of the illustrated rays from shifted signal 443 are passed by angle filter 449, however, ray 489 is not passed by angle filter 449 because its angle of incidence is outside the acceptable angle of incidence range that the angle filter 449 is configured for. Ray 489 was absorbed by filter 449 because of its relatively extreme angle of propagation compared to the plane of the pixels in the image pixel array 470. As described previously, blocking the more extreme angles of signal 443 may assist in resolving interference fringes in the interference pattern.

FIG. 5A illustrates a larger side view of an example angle filter 549 as an example of angle filter 449, in accordance with an embodiment of the disclosure. Angle filter 549 has a depth of dimension D1. The deeper the depth of dimension D1, the smaller the range of the accepted (passed) incident rays will be. FIG. 5B illustrates an example zoomed in plan view configuration of a portion of an example angle filter 549 that includes a plurality of honeycomb structures 585 having sides 588. If a ray (e.g. 489) encounters a side 588 of honeycomb structure 585, it is absorbed by an absorbing material coated on the sides 588 of honeycomb structure 585.

Figure 6:
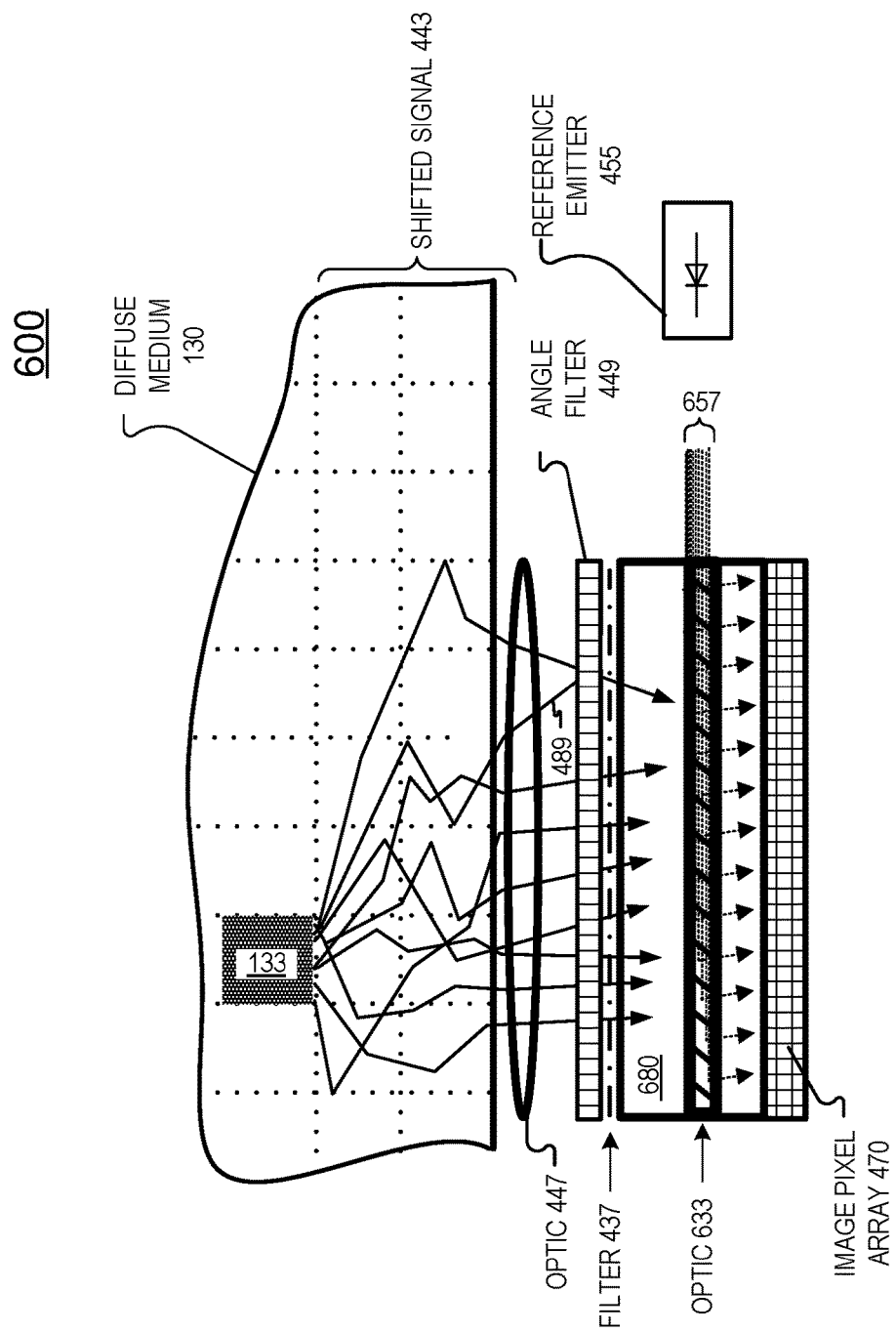
FIG. 6 illustrates an example imaging device having a lightguide optic for directing an infrared reference beam, in accordance with an embodiment of the disclosure.

FIG. 6 illustrates another imaging device including another example interference optic, in accordance with an embodiment of the disclosure. Device 600 includes some of the elements of device 400. In FIG. 6, partially reflective layer 483 is replaced by a lightguide optic 633. Lightguide optic 633 includes reflective features configured to redirect the infrared reference beam 657 to sensor 470 and lightguide optic 633 is further configured to pass wavelength-shifted exit signal 443 to sensor 470. Lightguide optic 633 may be configured to collimate the infrared reference beam 657 and direct rays of infrared reference beam 657 to sensor 470 at an angle relative to a vector that is normal to a pixel plane of the sensor 470. In some embodiments, the angle is between 4 and 8 degrees. In one embodiment, the angle is between 5 and 7 degrees.

Figure 7:
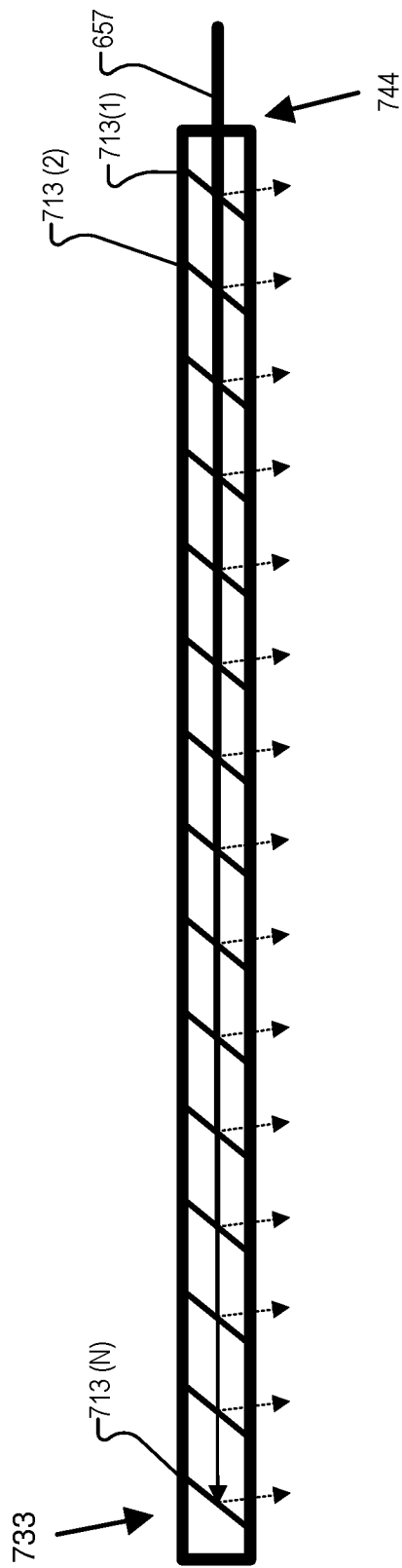
FIG. 7 illustrates a diagram illustration of an example lightguide optic, in accordance with an embodiment of the disclosure.

FIG. 7 illustrates a diagram illustration of a lightguide optic 733 that may be used as lightguide optic 633, in accordance with embodiments of the disclosure. Lightguide optic 733 is configured to receive infrared reference beam 657 at a receiving end 740 of the lightguide optic 733. FIG. 7 illustrates that lightguide optic 733 includes reflective features 713 configured to redirect the infrared reference beam 657 to the sensor 470. The reflective features 713 are progressively more reflective as a position of the reflective features gets farther from a receiving end 740 of the lightguide optic 733. The number N of reflective features is equal to fifteen in the diagram of FIG. 7, although N may be any number in different embodiments. The number N may be much larger than fifteen. Reflective element 713(N) is the last reflective feature while 713(1) is the first reflective feature, in FIG. 7. First reflective feature 713(1) is the first reflective feature encountered by beam 657. Since each reflective element reflects (and redirects) a portion of beam 657 to sensor 470, the intensity of beam 657 progressively decreases as it propagates through lightguide optic 733 and encounters the reflective features 713. The width of the illustrated beam 657 decreases in FIG. 7 as the beam propagates through lightguide optic 733 to indicate its decreasing intensity.

In one embodiment, each reflective feature 713 includes a slat that includes a partially mirrored layer that reflect a portion of infrared reference beam 657. In one embodiment, the first reflective feature 713(1) is a partially mirrored slat that reflects less than 10% beam 657 and the last reflective feature 713(N) is a mirror that approaches 100% reflectivity or is 100% reflective. Since the portion of beam 657 that encounters last reflective feature 713(N) will have already propagated through reflective features 713(1), 713(2) . . . 713(N−1), the intensity of the beam 657 received by last reflective feature 713(N) will be diminished compared to the intensity of the beam 657 received by first reflective feature 713(1). The reflectivity of each mirrored slat between feature 713(1) and 713(N) may progressively increase so that the redirected beam 657 (propagating toward the sensor 470) is of substantially uniform intensity across the image sensor.

In one embodiment, the reflective features 713 of lightguide optic 733 are fabricated using an ion implantation process in a silicon-on-insulator (SOI) waveguide. In one embodiment, lightguide optic 733 is fabricated by Himax Technologies, Inc.

In one embodiment, the reflective features 713 are implemented as portions of a two-dimensional Bragg gratings that are tuned to reflect (or partially reflect) the wavelength of beam 657 at the angle that beam 657 is received by the portion of the Bragg grating. In this embodiment, the Bragg grating is designed to be progressively more reflective as a position of the Bragg grating gets farther from the receiving end 740 of the lightguide optic.

The devices described in FIGS. 4 and 6 include interference optics that may reduce the depth of the device by providing a thinner optical solution to incouple infrared reference beam 657 to interfere with wavelength-shifted exit signal 443. The disclosed embodiments provided greatly reduced depth compared to a flat beam splitter oriented at 45 degrees from a pixel plane of an image sensor for incoupling beam 457/657, for example.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

Communication channels described in this disclosure may include wired or wireless communications utilizing IEEE 802.11 protocols, BlueTooth, SPI (Serial Peripheral Interface), I$^2$C (Inter-Integrated Circuit), USB (Universal Serial Port), CAN (Controller Area Network), cellular data protocols (e.g. 3G, 4G, LTE, 5G), or otherwise The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A device comprising:
   a sensor for measuring an infrared interference pattern;
   a coherent infrared illumination source configured to emit an infrared reference beam; and
   an optical structure configured to receive a wavelength-shifted exit signal, wherein the optical structure includes a partially reflective layer disposed on a curvature, and wherein the partially reflective layer redirects the infrared reference beam to the sensor,
   wherein the infrared interference pattern is generated by the wavelength-shifted exit signal interfering with the infrared reference beam, and wherein the wavelength-shifted exit signal encounters the partially reflective layer prior to becoming incident on the sensor.

2. The device of claim 1, wherein the curvature that the partially reflective layer is disposed on is a parabolic curvature.

3. The device of claim 2, wherein the parabolic curvature is configured to collimate the infrared reference beam and direct rays of the infrared reference beam to the sensor at an angle to a vector that is normal to a pixel plane of the sensor.

4. The device of claim 3, wherein the angle is between 4 and 8 degrees.

5. The device of claim 1 further comprising:
   an infrared filtering layer, wherein the partially reflective layer is disposed between the infrared filtering layer and the sensor, and wherein the infrared filtering layer is configured to pass a wavelength band of the wavelength-shifted exit signal and reject other light wavelengths.

6. The device of claim 5, wherein the infrared filtering layer is an angle-selective infrared filtering layer that is configured to transmit rays of the wavelength-shifted exit signal within an angle of incidence range and reject the rays of the wavelength-shifted exit signal that are outside of the angle of incidence range, and wherein the infrared filtering layer is disposed on a filtering plane that is parallel to a pixel plane of the sensor.

7. The device of claim 6, wherein incident rays that are greater than 10 degrees offset from a vector that is normal to the filtering plane are outside of the angle of incidence range.

8. The device of claim 5 further comprising:
   an angle filter optic configured to pass rays of the wavelength-shifted exit signal within an angle of incidence range and reject the rays of the wavelength-shifted exit signal that are outside of the angle of incidence range, wherein the partially reflective layer is disposed between the sensor and the angle filter optic.

9. The device of claim 8, wherein the angle filter optic includes a hexagonal honeycomb structure, and wherein a depth of the hexagonal honeycomb structure controls the angle of incidence range.

10. The device of claim 1, wherein the optical structure includes a refractive material disposed between the partially reflective layer disposed on the curvature and the sensor.

11. The device of claim 1, wherein the partially reflective layer is less than 30% reflective.

12. The device of claim 1, wherein the sensor includes a Complimentary Metal-Oxide-Semiconductor (CMOS) image pixel array.

13. The device of claim 1, wherein the infrared reference beam and the wavelength-shifted exit signal are a same wavelength.

* * * * *